US011432726B2

(12) United States Patent
Gigie et al.

(10) Patent No.: US 11,432,726 B2
(45) Date of Patent: Sep. 6, 2022

(54) REAL TIME UNOBTRUSIVE MONITORING OF PHYSIOLOGICAL SIGNALS

(71) Applicant: Tata Consultancy Services Limited, Mumbai (IN)

(72) Inventors: Andrew Gigie, Kolkata (IN); Smriti Rani, Kolkata (IN); Tapas Chakravarty, Kolkata (IN); Arijit Sinharay, Kolkata (IN); Arpan Pal, Kolkata (IN)

(73) Assignee: TATA CONSULTANCY SERVICES LIMITED

( * ) Notice: Subject to any disclaimer, the term of this patent is extended or adjusted under 35 U.S.C. 154(b) by 846 days.

(21) Appl. No.: 16/353,861

(22) Filed: Mar. 14, 2019

(65) Prior Publication Data
US 2020/0113445 A1 Apr. 16, 2020

(30) Foreign Application Priority Data
Oct. 10, 2018 (IN) .............................. 201821038470

(51) Int. Cl.
*A61B 5/0205* (2006.01)
*A61B 5/05* (2021.01)
(Continued)

(52) U.S. Cl.
CPC .............. *A61B 5/0205* (2013.01); *A61B 5/05* (2013.01); *A61B 5/1115* (2013.01);
(Continued)

(58) Field of Classification Search
CPC ....... A61B 5/0205; A61B 5/05; A61B 5/1115; A61B 5/7214; G01S 13/72; G01S 13/88
(Continued)

(56) References Cited

U.S. PATENT DOCUMENTS

| 6,553,098 B1* | 4/2003 | Harrison .................. H04B 3/46 |
| | | 379/1.04 |
| 9,867,013 B2* | 1/2018 | Nakata ................... H04B 1/385 |

(Continued)

FOREIGN PATENT DOCUMENTS

WO WO-2015/174879 11/2015

OTHER PUBLICATIONS

Li, C. et al. "Complex Signal Demodulation and Random Body Movement Cancellation Techniques for Non-contact Vital Sign Detection," *2008 IEEE MTT-S International Microwave Symposium Digest*, Atlanta, GA, Jun. 15-20, 2008; pp. 567-570.

*Primary Examiner* — Bo Fan
(74) *Attorney, Agent, or Firm* — Finnegan, Henderson, Farabow, Garrett & Dunner LLP

(57) ABSTRACT

This disclosure relates generally to methods and systems for real time unobtrusive monitoring of physiological signals of a subject confined to a bed. Output of single channel continuous wave (CW) radars are dependent upon distance of the subject from the radar. Dual channel IQ radars are more accurate but are costly and availability in the market is a constraint. The present disclosure provides a cheap and easily replicable pseudo IQ radar based system. The pseudo IQ radar comprises two CW radars placed at a calibrated distance from each other such that optimum points of one CW radar spatially overlaps null points of the other CW radar and phase imbalance is suppressed. Three such pseudo IQ radars are positioned in a predetermined configuration around the subject being monitored. A Supervised Complex Signal Demodulation (SCSD) method configured to suppress amplitude and DC imbalance is also provided for evaluating the physiological signals.

12 Claims, 10 Drawing Sheets

(51) Int. Cl.
  *A61B 5/11* (2006.01)
  *A61B 5/00* (2006.01)
  *G01S 13/88* (2006.01)
  *G01S 13/72* (2006.01)

(52) U.S. Cl.
  CPC ............ *A61B 5/7214* (2013.01); *G01S 13/72* (2013.01); *G01S 13/88* (2013.01)

(58) Field of Classification Search
  USPC ...... 600/301, 407; 702/191; 342/28, 109, 84
  See application file for complete search history.

(56) References Cited

U.S. PATENT DOCUMENTS

| | | | |
|---|---|---|---|
| 2008/0119716 A1* | 5/2008 | Boric-Lubecke .... | A61B 5/7225 600/407 |
| 2012/0209087 A1* | 8/2012 | Horng .................... | G01S 13/87 600/301 |
| 2018/0078166 A1* | 3/2018 | Horng ................. | A61B 5/7225 |

* cited by examiner

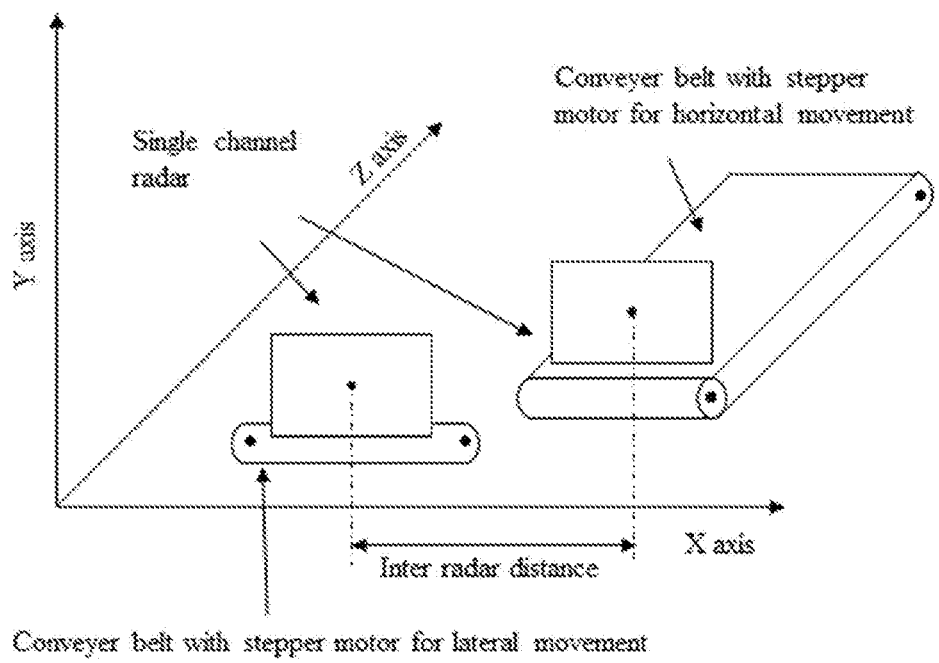
FIG.5A
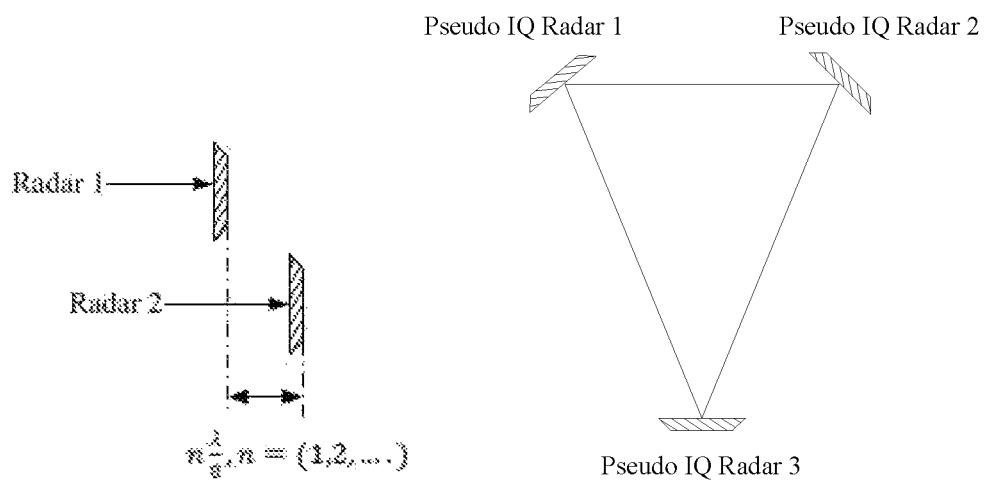
FIG.5B
FIG.5C

REAL TIME UNOBTRUSIVE MONITORING OF PHYSIOLOGICAL SIGNALS

PRIORITY CLAIM

This U.S. patent application claims priority under 35 U.S.C. § 119 to: Indian Patent Application No. 201821038470, filed on 10 Oct. 2018. The entire contents of the aforementioned application are incorporated herein by reference.

TECHNICAL FIELD

The disclosure herein generally relates to unobtrusive monitoring of physiological signals, and, more particularly, to real time and cost effective unobtrusive monitoring.

BACKGROUND

Microwave radar technology is being exploited these days for detecting minute vibrations including heart rates and breathing rates. However, microwave interferometry suffers from some issues that may corrupt the measurements, if not handled properly. One of such issues arises from the relation between vibrational amplitudes and the probing wavelength when measurements are done through standard radar baseband processing, sometimes termed as microwave interferometry. If the vibrational amplitude increases in terms of displacement over a certain threshold (compared to the probing wavelength) then the baseband measurement contains harmonics that can often mislead the measurement. This can be managed by maintaining a suitable amplitude vs wavelength ratio. However, the measurement can still suffer from harmonics if measuring around null-points. The situation becomes more problematic in cases where the radar module cannot be fixed at a desirable position (i.e. at optimal point) but requires treading on the move (say hand-held unit for detecting vibrations). Similarly, for use-cases where the subject is also not rigidly bound to a specific point (say non-contact heart-rate or breathing monitoring where people can comfortably stand or sit in front of a fixed radar), the null-point issues may arise and can lead to erroneous measurements. Moreover, measurement around null-point not only creates harmonics but also suffers from sharp decrease in sensitivity. To overcome such issues related to null-points, IQ channel radars are used. However, cost and availability in the market of IQ radars is a major bottleneck in its utilization.

SUMMARY

Embodiments of the present disclosure present technological improvements as solutions to one or more of the above-mentioned technical problems recognized by the inventors in conventional systems.

In an aspect, there is provided a processor implemented method for real time unobtrusive monitoring of physiological signals pertaining to a subject confined to a bed, the method comprising the steps of: obtaining periodically, by one or more hardware processors, a motion data signal pertaining to the physiological signals including heartbeat rate and breathing rate from the subject, from a pseudo I (in-phase) channel and a pseudo Q (in quadrature) channel of three pseudo IQ radars, wherein the three pseudo IQ radars are positioned in a predetermined configuration around the subject and wherein each of the three pseudo IQ radars comprise a pair of single channel continuous wave (CW) radars placed at a calibrated distance from each other such that optimum points of one CW radar in the pair spatially overlaps null points of the other CW radar in the pair, a baseband signal from the CW radars constituting the pair serving as the pseudo I channel and the pseudo Q channel respectively; processing, by the one or more hardware processors, the motion data signal from each of the three pseudo IQ radars, to discard the motion data signal having motion artifacts; determining, by the one or more hardware processors, Quality of Information (QOI) based on at least one of Signal to Noise Ratio (SNR) and frequency spectrum associated with the motion data signal from each of the three pseudo IQ radars having no motion artifacts, wherein the QoI is indicative of the pseudo IQ radar from the three pseudo IQ radars to be considered for each lying position of the subject such that readings corresponding to the motion data signal have maximum SNR and minimum harmonic content; recalibrating, by the one or more hardware processors, one or more of the three pseudo IQ radars if the readings corresponding to the motion data signal having no motion artifacts deviate from an empirically determined threshold, wherein the threshold is indicative of number of times anomalous readings are received from the pseudo I channel and the pseudo Q channel; and evaluating, by the one or more hardware processors, the heartbeat rate and breathing rate by applying a Supervised Complex Signal Demodulation (SCSD) method on the motion signal data received from the one or more of the three pseudo IQ radars based on the QoI, wherein the SCSD method is configured to suppress amplitude and DC imbalance by assigning weights to the pseudo I channel and the pseudo Q channel, the weights being determined using a simulated trained weighted K-Nearest Neighbor (KNN) model configured to identify reliability of the pseudo I channel and the pseudo Q channel based on Fast Fourier Transform (FFT) pattern thereof in the range of the heartbeat rate and breathing rate, the reliability being indicative of harmonic content in the motion signal data.

In another aspect, there is provided a system for real time unobtrusive monitoring of physiological signals pertaining to a subject confined to a bed, the system comprising an indented radar system comprising three pseudo IQ radars positioned in a predetermined configuration around the subject, wherein each of the three pseudo IQ radars comprises a pair of single channel continuous wave (CW) radars placed at a calibrated distance from each other such that optimum points of one CW radar in the pair spatially overlaps null points of the other CW radar in the pair, a baseband signal from the CW radars constituting the pair serving as a pseudo I (in-phase) channel and a pseudo Q (in quadrature) channel respectively; and a controller unit in communication with each of the three pseudo IQ radars, wherein the controller unit comprises: one or more data storage devices configured to store instructions; and one or more hardware processors operatively coupled to the one or more data storage devices, wherein the one or more hardware processors are configured by the instructions to: obtaining periodically, a motion data signal pertaining to the physiological signals including heartbeat rate and breathing rate from the subject, from the pseudo I channel and the pseudo Q channel of the three pseudo IQ radars; processing the motion data signal from each of the three pseudo IQ radars, to discard the motion data signal having motion artifacts; determining Quality of Information (QoI) based on at least one of Signal to Noise Ratio (SNR) and frequency spectrum associated with the motion data signal from each of the three pseudo IQ radars having no motion artifacts, wherein the QoI is indicative of the pseudo IQ radar from the three pseudo IQ radars to be considered for each lying position of the subject such that readings corresponding to the motion data signal have maximum SNR and minimum harmonic content; recalibrating one or more of the three pseudo IQ radars if the readings corresponding to the motion data signal having no motion artifacts deviate from an empirically determined threshold, wherein the threshold is indicative of number of times anomalous readings are received from the pseudo I channel and the pseudo Q channel; and evaluating the heartbeat rate and breathing rate by applying a Supervised Complex Signal Demodulation (SCSD) method on the motion signal data received from the one or more of the three pseudo IQ radars based on the QoI, wherein the SCSD method is configured to suppress amplitude and DC imbalance by assigning weights to the pseudo I channel and the pseudo Q channel, the weights being determined using a simulated trained weighted K-Nearest Neighbor (KNN) model configured to identify reliability of the pseudo I channel and the pseudo Q channel based on Fast Fourier Transform (FFT) pattern thereof in the range of the heartbeat rate and breathing rate, the reliability being indicative of harmonic content in the motion signal data.

In an embodiment of the present disclosure, the predetermined configuration provides maximum beam coverage of the bed and comprises two of the three pseudo IQ radars positioned over the subject and one of the three pseudo IQ radars positioned below the bed such that the three pseudo IQ radars form an isosceles triangle for obtaining the motion data signal unobtrusively regardless of the lying position of the subject on the bed.

In an embodiment of the present disclosure, the calibrated distance is based on wavelength of the CW radars comprising the three pseudo IQ radars.

In an embodiment of the present disclosure, the calibrated distance is an integer (n) multiple of one eighth of the wavelength ($\lambda/8$) of the CW radars comprising the three pseudo IQ radars.

In an embodiment of the present disclosure, the presence of motion artifacts is detected when dominant frequency in the motion signal data is beyond 2 Hz.

In an embodiment of the present disclosure, the one or more hardware processors are further configured by the instructions to perform recalibrating one or more of the three pseudo IQ radars by suppressing phase imbalance between the pseudo I channel and the pseudo Q channel by fine adjustment of the calibrated distance between the CW radars constituting the pair.

In an embodiment of the present disclosure, the one or more hardware processors are further configured by the instructions to perform training of the simulated trained weighted K-Nearest Neighbor (KNN) model using training data simulated by: dividing the calibrated distance into a plurality of bins including points ranging from the optimum points to the null points; further dividing each of the plurality of bins into five classes including null class, better null class, middle class, better optimum class and optimum class having a distinct frequency spectrum therein; identifying a frequency band of operation corresponding to the physiological signal being monitored; simulating for each of the five classes comprised in each of the plurality of bins, the baseband signal for incremental steps of all frequencies in the frequency band of operation and incremental distances corresponding to each of the five classes; generating features including location of peaks and peak to peak ratio from frequency plots using the simulated baseband signal for each of the five classes comprised in each of the plurality of bins; and training the weighted KNN model using the generated features for each of the five classes comprised in each of the plurality of bins It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 5A and FIG. 5B illustrate a front view and a top view respectively of a pseudo IQ radar, in accordance with an embodiment of the present disclosure.

FIG. 5C illustrates triangulation of three pseudo IQ radars forming the system of the present disclosure.

DETAILED DESCRIPTION OF EMBODIMENTS

Figure 1:
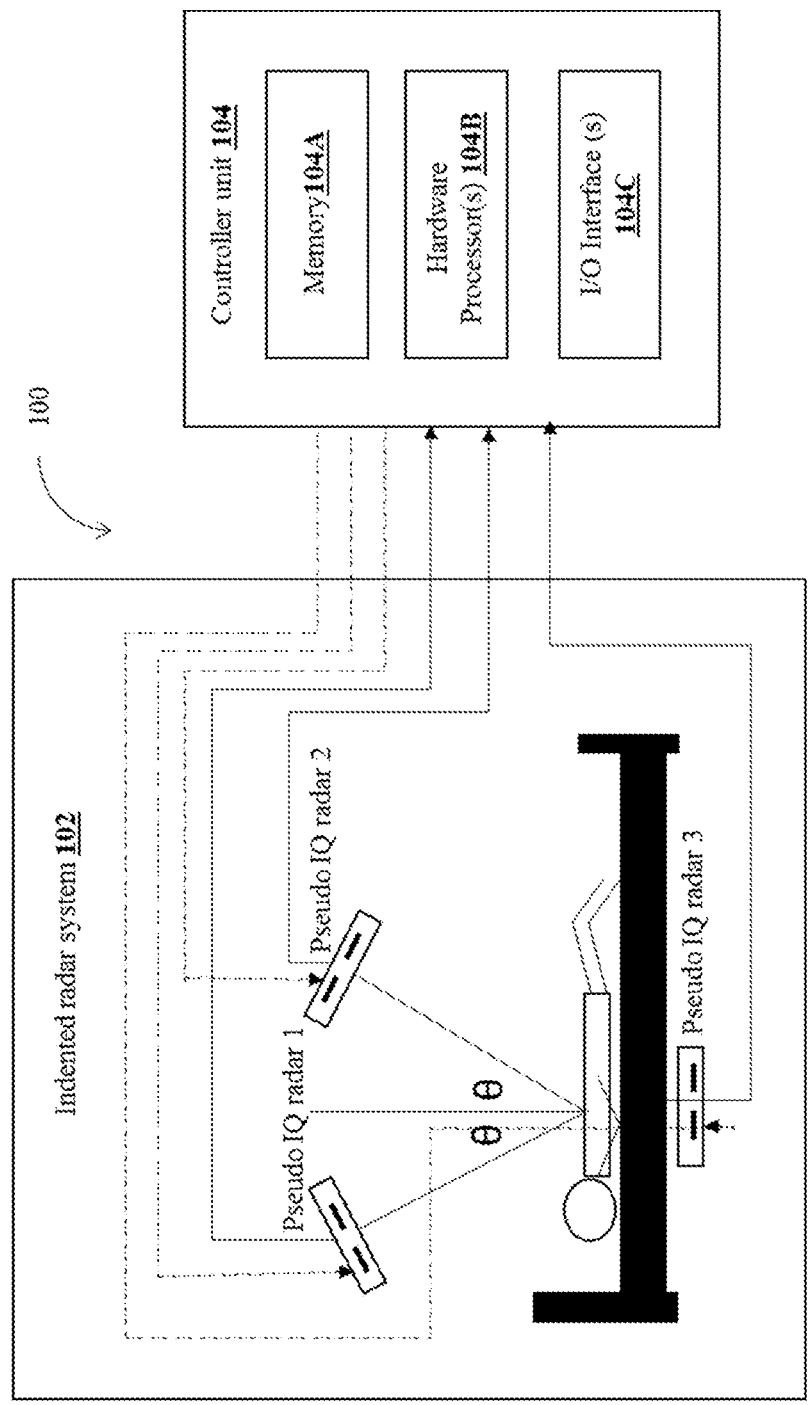
FIG. 1 illustrates an exemplary block diagram of a system for real time unobtrusive monitoring of physiological signals, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

In applications, where distance between the radar and target is not fixed, single channel radars face a problem of null-point. Thus, most of the prior-arts related to vibration detection involve using a Quadrature (IQ channel) radar. However, IQ radar is a costly solution and the relative inadequacy of such radars in the market puts constraints in scaling to a feasible solution. An effective way around is to use two single channel radars that are offset in space by difference in path-length (corresponding to 90-degree phase-shift provided by a local oscillator) to act approximately as an IQ radar. However, a system having two independent radars with a spatial offset between them is more prone to different imbalances such as amplitude, phase and DC. Hence, using the straight forward Complex Signal Demodulation (CSD) or Differentiate And Cross Multiply (DACM) methods, frequently used with standard IQ radars, fails in many situations if these are used as is on a two-radar system.

Referring now to the drawings, and more particularly to FIG. 1 through FIG. 9D, where similar reference characters denote corresponding features consistently throughout the figures, there are shown preferred embodiments and these embodiments are described in the context of the following exemplary system and/or method.

Figure 2A:
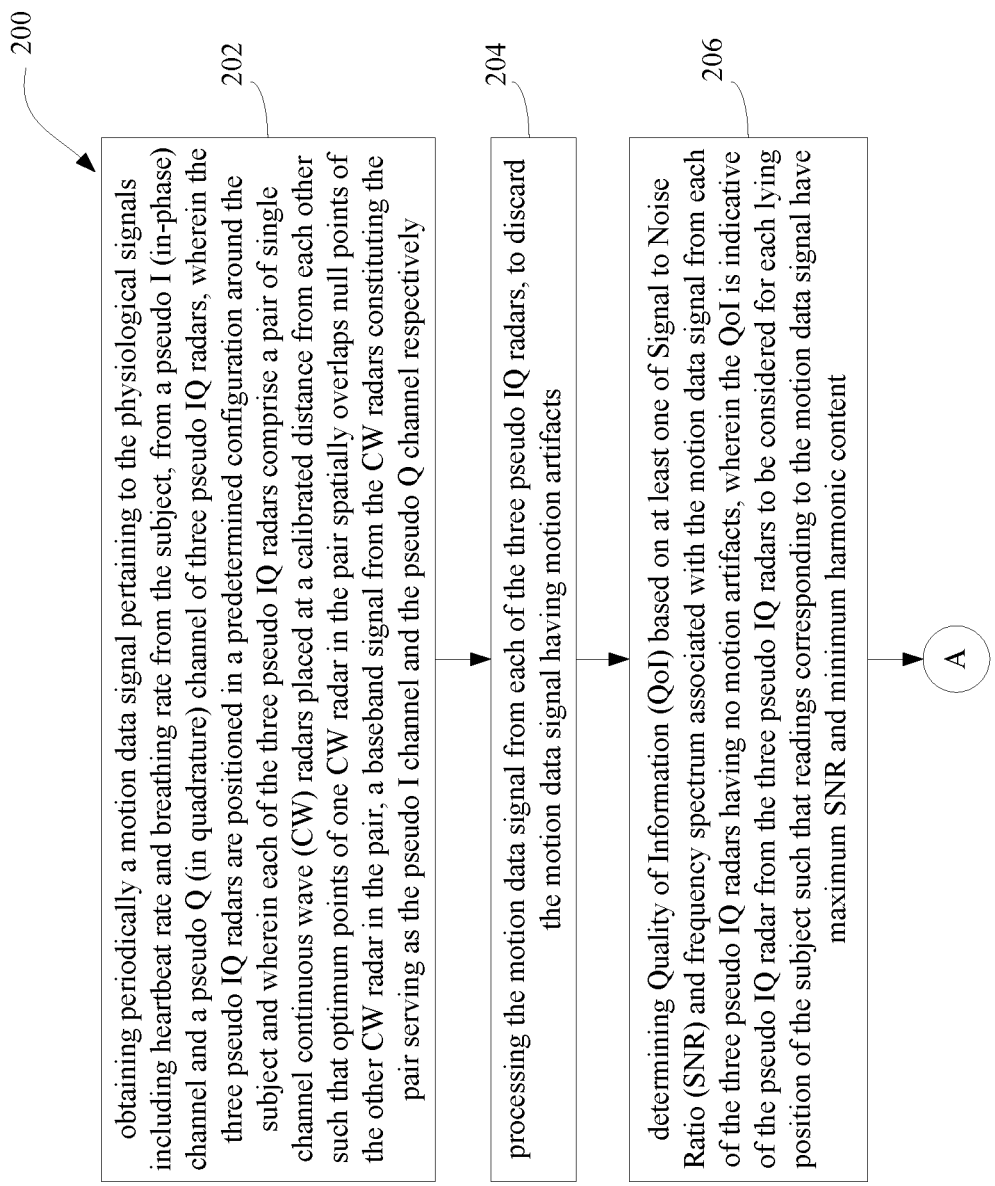
FIG. 2A through FIG. 2B is an exemplary flow diagram illustrating a computer implemented method for real time unobtrusive monitoring of physiological signals, in accordance with an embodiment of the present disclosure.
Figure 2B:
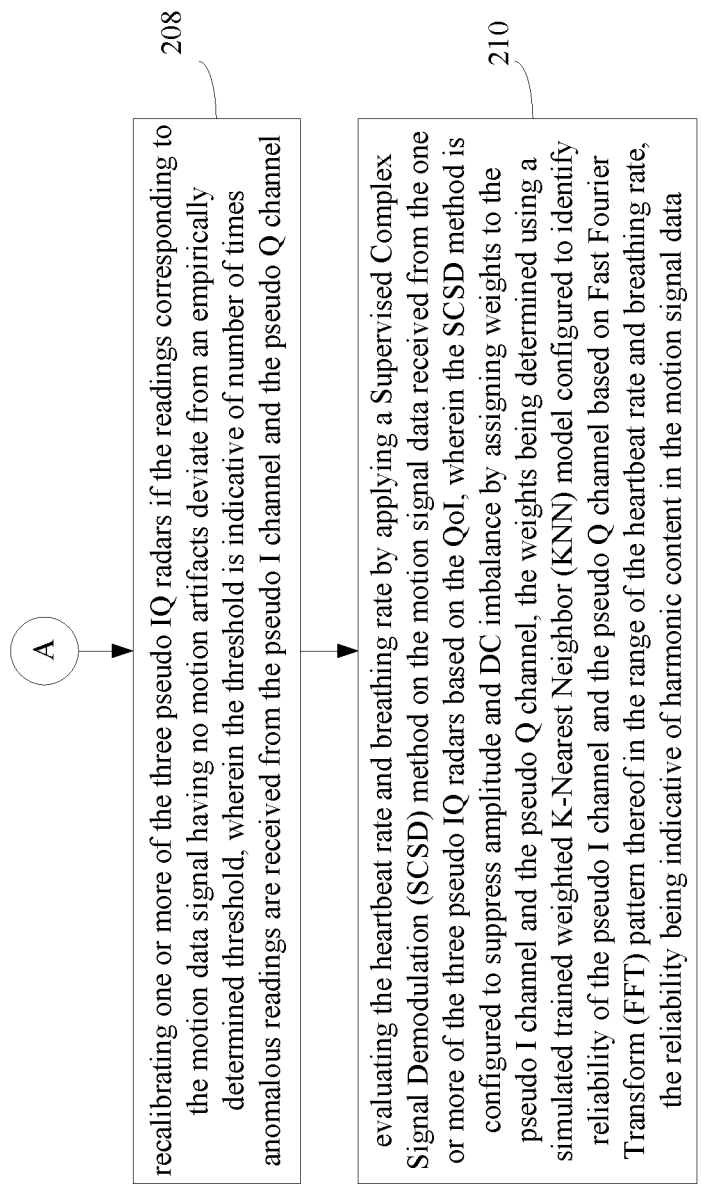

FIG. 1 illustrates an exemplary block diagram of a system 100 for real time unobtrusive monitoring of physiological signals pertaining to a subject confined to a bed, in accordance with an embodiment of the present disclosure. FIG. 2A through FIG. 2B is an exemplary flow diagram illustrating a computer implemented method 200 for real time unobtrusive monitoring of physiological signals, in accordance with an embodiment of the present disclosure. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In an embodiment, the system 100 comprises an indented radar system 102 that includes three pseudo IQ radars positioned in a predetermined configuration around the subject. In accordance with the present disclosure, each of the three pseudo IQ radars comprise a pair of single channel continuous wave (CW) radars placed at a calibrated distance from each other such that optimum points of one CW radar in the pair spatially overlaps null points of the other CW radar in the pair. In accordance with the present disclosure, a baseband signal from the CW radars constituting the pair serve as a pseudo I (in-phase) channel and a pseudo Q (in quadrature) channel respectively.

Figure 3:
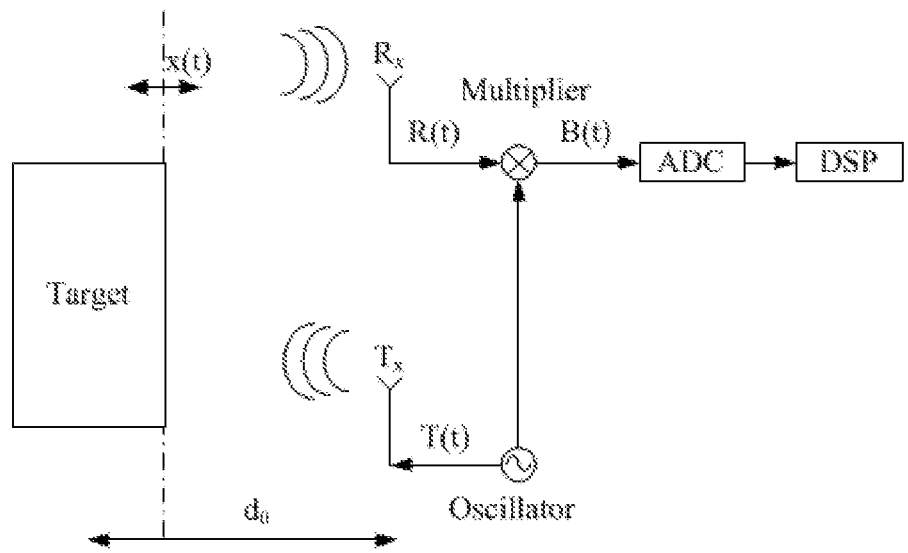
FIG. 3 illustrates a block diagram of a continuous wave (CW) radar as known in the art.

FIG. 3 illustrates a block diagram of a continuous wave (CW) radar as known in the art. An oscillator generates a single tone high frequency signal T(t) of frequency f and wavelength λ. The signal T(t) is then transmitted into space using a transmitter antenna (Tx). Let, a vibrating target, which is at a distance $d_o$ from the radar, be undulating in simple harmonic motion, x(t) with frequency f. The displacement of the vibrating target modulates the transmitted signal and a part of this signal gets reflected back to the CW radar. This reflected signal is captured by a receiver antenna (Rx). The received echo signal R(t) is then mixed with local oscillator signal T(t) from the transmitter (Tx) and the resultant signal is passed through a low pass filter to filter out the baseband signal B(t). The equation of the baseband signal B(t) is as shown in equation (1) below.

$$B(t) = \cos\left(\theta_0 + \frac{4\pi x(t)}{\lambda} + \Delta\theta(t)\right) \quad (1)$$

$$\text{where } \theta_0 = \frac{4\pi d_0}{\lambda} \quad (2)$$

$$\text{and } x(t) = A\sin(2\pi f t) \quad (3)$$

$$\Delta\theta(t) = \theta(t) - \theta\left(t - \frac{d_0}{c}\right) \quad (4)$$

Equation (2) represents a constant phase due to the fixed distance of the vibrating object from the radar. Equation (3) depicts vibration frequency of the target. $\Delta\theta(t)$ in equation (4) represents a difference in phase noise from the local oscillator, for the transmitter and the receiver respectively. It is usually considered to be negligible for short range application in a quadrature radar. For a body, vibrating at a fixed distance, $\theta_0$ is constant. In the indented radar setup, A $\Delta\theta(t)$ is no longer negligible, as two separate single channel radars are used to replicate an IQ Radar.

Figure 4:
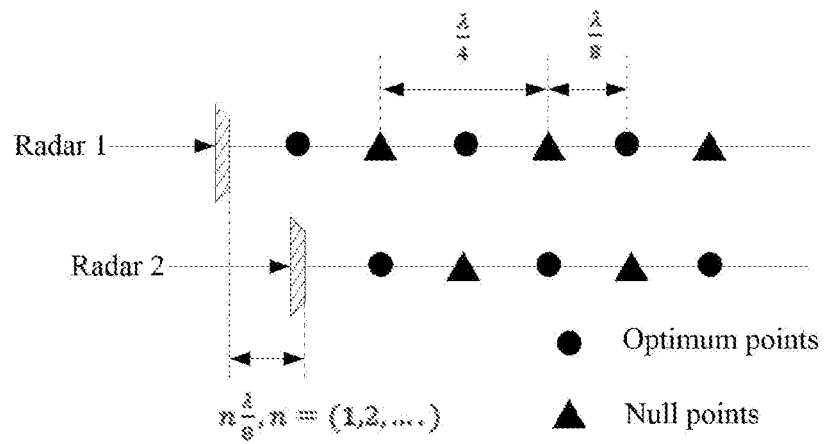
FIG. 4 illustrates null points and optimum points of two single channel radars separated by a calibrated distance from each other, in accordance with an embodiment of the present disclosure.

In a Quadrature radar, I and Q outputs are generated by providing a 90 degree phase shift to the oscillator frequency and then mixing with the received echo signal. FIG. 4 illustrates null points and optimum points of two single channel radars (CW) separated by a calibrated distance from each other based on wavelength of the CW radars, in accordance with an embodiment of the present disclosure. For the indented radar system 102, I and Q outputs are generated by spatially separating the two single channel radars (CW) by the calibrated distance equal to integer (n) multiples of the wavelength λ/8.

In accordance with the present disclosure, for the indented radar system of FIG. 4, equation (1) is rewritten for both the channels as:

$$B_I(t) = \cos\left(\theta_0 + \frac{4\pi x(t)}{\lambda} + \Delta\theta(t)\right) \quad (5)$$

and $$B_Q(t) = \cos\left(\frac{4\pi(d_0 - \lambda/8)}{\lambda} + \frac{4\pi x(t)}{\lambda} + \Delta\theta(t)\right) \quad (6)$$

Equation (6) may be re-written as $$B_Q(t) = \cos\left(\theta_0 - \frac{\pi}{2} + \frac{4\pi x(t)}{\lambda} + \Delta\theta(t)\right) \quad (7)$$

or $$B_Q(t) = \sin\left(\theta_0 + \frac{4\pi x(t)}{\lambda} + \Delta\theta(t)\right) \quad (8)$$

Thus equations (5) and (8) form the pseudo I channel and the pseudo Q channel for the indented radar system 102 of the present disclosure.

In an embodiment of the present disclosure, the system 100 further comprises a controller unit 104 in communication with each of the three pseudo IQ radars of the indented radar system 102. In an embodiment, the controller unit 104 includes one or more data storage devices or memory 104A configured to store instructions and one or more hardware processors 104B operatively coupled to the one or more data storage devices 1048, wherein the one or more hardware processors are configured for execution of steps of the method 200 of FIG. 2A and FIG. 2B. The one or more processors 104B that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

In an embodiment, the system 100 includes communication interface device(s) or input/output (I/O) interface(s) 106 (not shown). The I/O interface(s) 106 may include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 104A may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 may be stored in the memory 104A.

In accordance with an embodiment of the present disclosure, the one or more processors 104B are configured to obtain periodically, at step 202, a motion data signal pertaining to the physiological signals such as heartbeat rate and breathing rate of the subject being monitored from the pseudo I channel and the pseudo Q channel of the three pseudo IQ radars of the indented radar system 102.

In accordance with an embodiment of the present disclosure, the one or more processors 104B are configured to process, at step 202, the motion data signal from each of the three pseudo IQ radars, to discard the motion data signal having motion artifacts. The presence of motion artifacts is detected when dominant frequency in the motion signal data is beyond 2 Hz, considering the breathing rate and heart rate are limited to 0.2-0.4 Hz and 1-2 Hz, respectively.

In accordance with an embodiment of the present disclosure, the one or more processors 1048 are configured to determine, at step 206, Quality of Information (QoI) based on at least one of Signal to Noise Ratio (SNR) and frequency spectrum associated with the motion data signal from each of the three pseudo IQ radars having no motion artifacts. In accordance with the present disclosure, the QoI is indicative of the pseudo IQ radar from the three pseudo IQ radars that needs to be considered for each lying position of the subject such that readings corresponding to the motion data signal have maximum SNR and minimum harmonic content. The QoI for different positions of the subject may be represented as shown in the Table 1 below.

TABLE 1

Typical values of QoI

| | Subject lying on back/front | Subject lying on side facing pseudo IQ radar 2 | Subject lying on side facing pseudo IQ radar 1 |
|---|---|---|---|
| Pseudo IQ radar 3 | Best | Bad | Bad |
| Pseudo IQ radar 1 | Better | Best | Better |
| Pseudo IQ radar 2 | Better | Better | Best |

As stated above, the three pseudo IQ radars are positioned in the predetermined configuration around the subject and the calibrated distance between the pair of CW radars comprising each of the three IQ radars is $n\lambda/8$. FIG. 5A and FIG. 5B illustrate a front view and a top view respectively of the pseudo IQ radar, in accordance with an embodiment of the present disclosure. It is possible that the CW radars in each pair may not be perfected placed at the $n\Delta/8$ distance due to distance imperfections, background clutter, and the like and accordingly, the phase difference may be ±10 deg. In accordance with an embodiment of the present disclosure, this may be corrected by placing the CW radars on adjusting means which allow for horizontal and lateral movements respectively. In an embodiment, conveyer belt with stepper motor may be provided for the horizontal and lateral movements as illustrated in FIG. 5A. FIG. 5B illustrates the inter radar distance ($n\lambda/8$).

In an embodiment of the present disclosure, the predetermined configuration of the indented radar system 102 provides maximum beam coverage of the bed by positioning two of the three pseudo IQ radars over the subject and one of the three pseudo IQ radars below the bed as illustrated in FIG. 1. FIG. 5C illustrates triangulation of three pseudo IQ radars forming the system of the present disclosure. The three pseudo IQ radars are placed in the predetermined configuration forming the isosceles triangle as illustrated for better accuracy in monitoring the physiological signals by obtaining the motion data signal unobtrusively regardless of the lying position of the subject on the bed.

Figure 6:
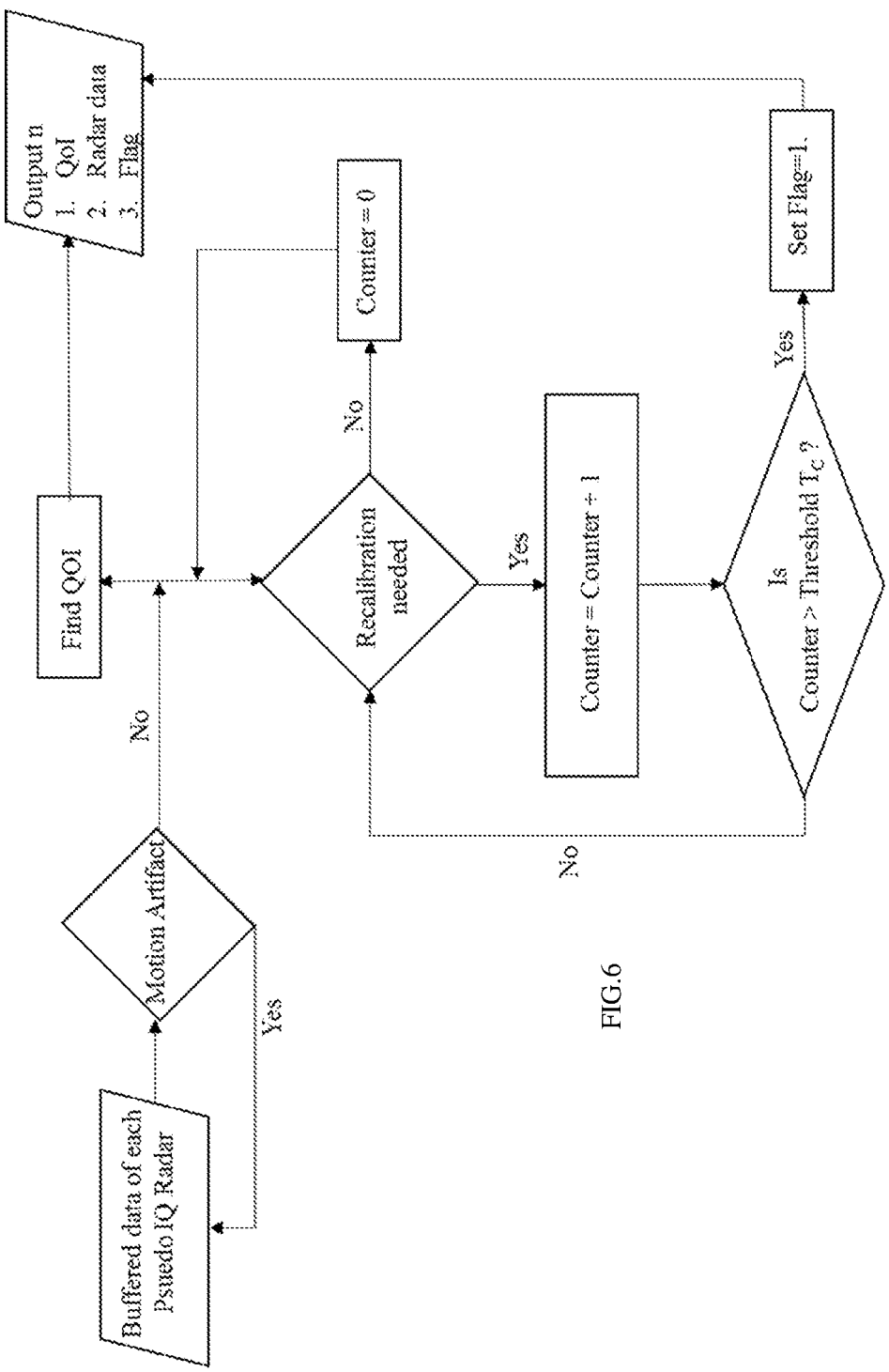
FIG. 6 illustrates a schematic presentation of the output block for each of the three IQ radars, in accordance with an embodiment of the present disclosure.

FIG. 6 illustrates a schematic presentation of the output block for each of the three pseudo IQ radars, in accordance with an embodiment of the present disclosure. In an embodiment, buffered data from each of the three pseudo IQ radars are used to check for motion artifacts at step 204. In an embodiment, wherein the subject is a human, motion speed above 2 Hz in Doppler frequency may be considered. Table 2 below indicates moving speed and corresponding Doppler frequency for reference.

TABLE 2

| Transmitting frequency (Frequency of CW radar) (Hz) | Moving speed (m/s) | Doppler frequency (Hz) |
|---|---|---|
| 10525000000 | 0.028 | 1.39 |
| 10525000000 | 0.25 | 12.40 |
| 10525000000 | 0.5 | 24.81 |
| 10525000000 | 0.71 | 35.23 |
| 10525000000 | 0.9 | 44.65 |
| 10525000000 | 1 | 49.62 |
| 10525000000 | 1.15 | 57.06 |
| 10525000000 | 1.25 | 62.02 |
| 10525000000 | 1.42 | 70.45 |
| 10525000000 | 1.75 | 86.83 |
| 10525000000 | 2 | 99.23 |
| 10525000000 | 2.5 | 124.04 |
| 10525000000 | 3 | 148.85 |

In an embodiment wherein the subject is a human, if the Doppler frequency is 2 Hz, the subject is lying motionlessly on the bed. When the person moves, motion artifacts are detected at step 204 and the buffered data is discarded. After checking for motion artifacts, the buffered data is then used to determine the QoI at step 206. QoI basically indicates whether the quality of the motion data signal is good for detecting the heart rate and the breathing rate based on at least the SNR and harmonic content as explained above.

In accordance with an embodiment of the present disclosure, the one or more processors 104B are configured to recalibrate, at step 208, one or more of the three pseudo IQ radars if the readings corresponding to the motion data signal having no motion artifacts deviate from an empirically determined threshold, wherein the threshold is indicative of number of times anomalous readings are received from the pseudo I channel and the pseudo Q channel. The need for recalibrating involves checking whether the CW radars comprised in each of the three pseudo IQ radars are calibrated correctly to serve as I channel and Q channel. If an anomaly is detected in terms of the readings (also referred interchangeably as radar data) corresponding to the motion data signal deviating from the empirically determined threshold (Tc), a flag for the corresponding pseudo IQ radar is set to 1 indicating that particular pseudo IQ radar needs to be recalibrated. After each of the three pseudo IQ radar's flags and QoI information is generated, recalibration, at step 208, may be initiated. In accordance with the present disclosure, the step 208 of recalibrating suppresses phase imbalance between the pseudo I channel and the pseudo Q channel by fine adjustment of the calibrated distance between the CW radars constituting the pair.

Figure 7:
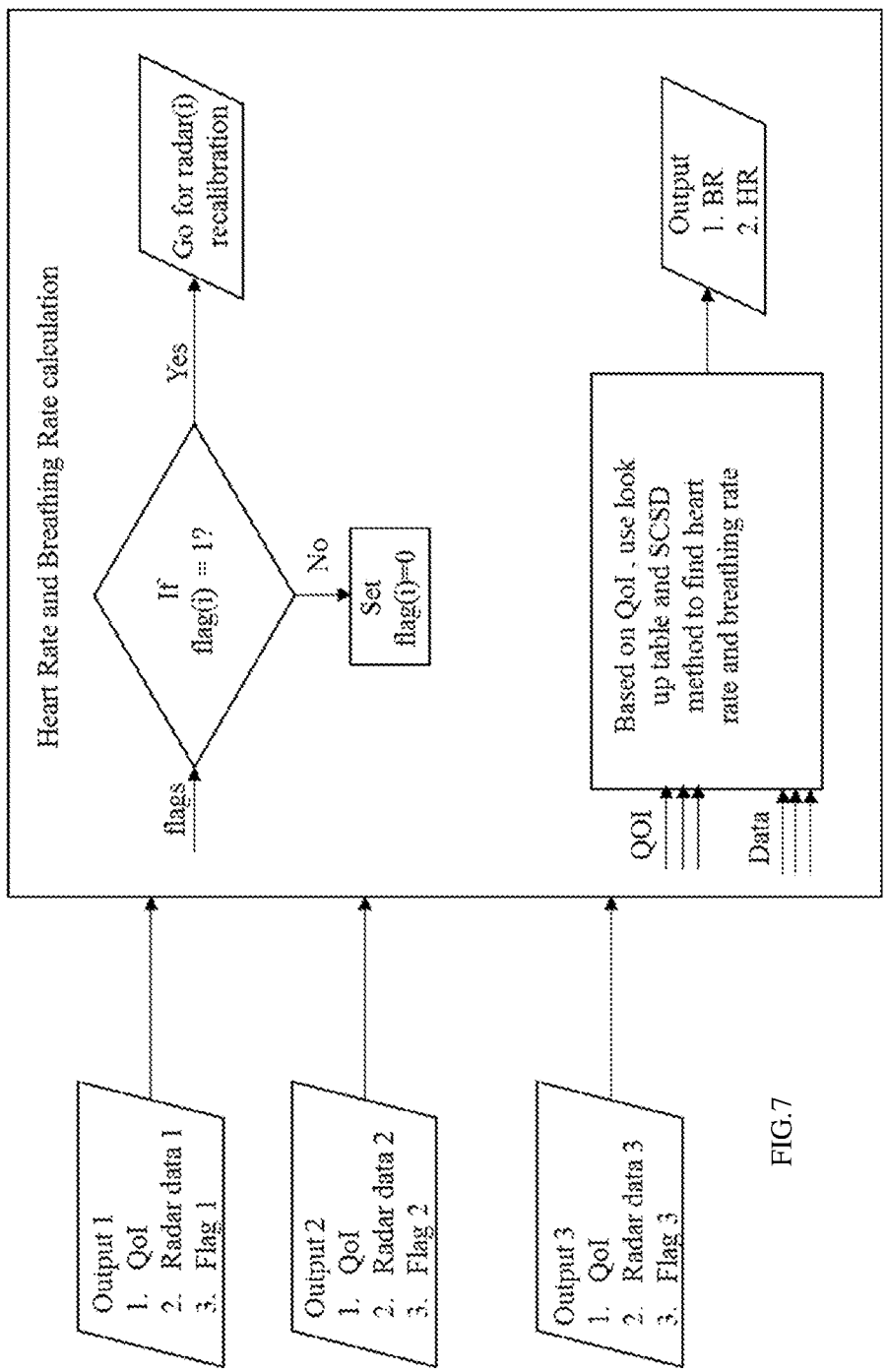
FIG. 7 illustrates a schematic representation of consolidation of the output from each of the three IQ radars, in accordance with an embodiment of the present disclosure.

FIG. 7 illustrates a schematic representation of consolidation of the output from each of the three IQ radars, in accordance with an embodiment of the present disclosure. A Supervised Complex Signal Demodulation (SCSD) method, in accordance with an embodiment of the present disclosure is applied to the motion signal data having a good QoI value as determined from the Table 1. Weights obtained from a simulated trained model are then provided to the pseudo I channel and the pseudo Q channel. The simulated trained model is capable of identifying reliability of the channel based on its Fast Fourier Transform (FFT) pattern in the range of the physiological signal being monitored (heart rate and breathing rate). Accordingly, in an embodiment, the one or more processors 104B are configured to evaluate, at step 210, the heartbeat rate and breathing rate by applying the SCSD method on the motion signal data received from the one or more of the three pseudo IQ radars based on the QoI, wherein the SCSD method is configured to suppress amplitude and DC imbalance by assigning weights to the pseudo I channel and the pseudo Q channel, the weights being determined using a simulated trained weighted K-Nearest Neighbor (KNN) model configured to identify reliability of the pseudo I channel and the pseudo Q channel based on the FFT pattern of the channel in the range of the heartbeat rate and breathing rate. In accordance with the present disclosure, the reliability is indicative of harmonic content in the motion signal data.

Figure 8:
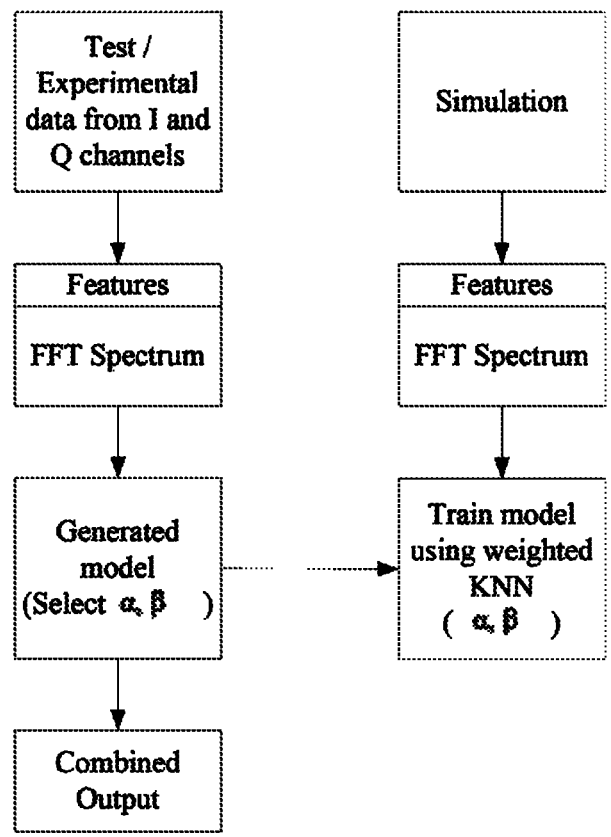
FIG. 8 illustrates a schematic representation of a Supervised Complex Signal Demodulation (SCSD) method, in accordance with an embodiment of the present disclosure.

FIG. 8 illustrates a schematic representation of the SCSD method, in accordance with an embodiment of the present disclosure. The CSD equation, as known in the art is as shown in equation (9) below.

$$B_I(t) + jB_Q(t) = \cos\left(\theta_0 + \frac{4\pi x(t)}{\lambda}\right) + j \sin\left(\theta_0 + \frac{4\pi x(t)}{\lambda}\right) \quad (9)$$

In accordance with the present disclosure, wherein pseudo IQ radars are implemented, amplitude and DC imbalances are bound to happen in real time. By simulating different scenarios of mismatch (amplitude and DC), it was found that the effect of amplitude mismatch is significant. Hence the effect of amplitude imbalance is addressed by the SCSD method of the present disclosure, wherein the equation (9) is modified as equation (10) given below.

$$B_I(t) + jB_Q(t) = A_i\cos\left(\theta_0 + \frac{4\pi x(t)}{\lambda}\right) + j A_q\sin\left(\theta_0 + \frac{4\pi x(t)}{\lambda}\right) \quad (10)$$

wherein $A_i$ and $A_q$ represent the amplitude mismatch between the two channels. Ideally, the CSD method is independent of distance between the radar and the target and the same frequency spectrum may be expected for a given vibrating target at any distance. Accordingly, the same frequency spectrum may be expected at any distance for the combined output from the pseudo IQ radars and the Signal strength (SNR) at null position is expected to be far less compared to optimum position. However, due to amplitude mismatch, this may not always be true. The effect of amplitude imbalance on CSD output is obtained by simulating equation (10).

In accordance with an embodiment of the present disclosure, the simulated trained weighted K-Nearest Neighbor (KNN) model is trained using training data simulated by firstly dividing the calibrated distance into a plurality of bins including points ranging from the optimum points to the null points. Each of the plurality of bins is further subdivided into five classes labelled as null class, better null class, middle class, better optimum class and optimum class. These classes are selected such that the frequency pattern is distinct in each of them. At any distance, either the pseudo I channel or the pseudo Q channel captures a better estimation of the fundamental frequencies associated with the subject, wherein the heart rate and the breathing rate provide the vibrating signals. A frequency band of operation corresponding to the physiological signal being monitored is identified. For, each of the five classes comprised in each of the plurality of bins, the baseband signal is simulated for incremental steps of all frequencies in the frequency band of operation and incremental distances corresponding to each of the five classes. Based on the frequency pattern of the motion data signal received, the supervised learning model using the weighted KNN method is generated to allocate a closest resemblance class for the received motion data signal. The features for the model are based on the peaks and peak to peak ratio from frequency plots using the simulated baseband signal for each of the five classes comprised in each of the plurality of bins. The weighted KNN model is trained using the generated features for each of the five classes comprised in each of the plurality of bins.

In a testing phase, features obtained from the experimental data pseudo I and the pseudo Q channel is fed separately to the trained weighted KNN model. After discerning the label, the trained weighted KNN model assigns α and β value to the pseudo I channel and the pseudo Q channel respectively. Nearer the frequency pattern, to the optimum bin, more is the α or β value. The classes and their corresponding α or β value are shown in Table 3 below.

TABLE 3

| Class | Null | Better null | Middle | Better optimum | Optimum |
|---|---|---|---|---|---|
| α or β | 0 | 0.25 | 0.5 | 0.75 | 1 |

After the α and β values are assigned for both the channels, the output is combined using equation (11) given below.

$$B(t) = \alpha I + J\beta Q \qquad (11)$$

Since the SCSD method considers both the channels independent of each other while assigning the class label and more weight is given to the signal having resemblance to the optimum position, the problem of amplitude and DC offset variations are addressed.

Experimental Evaluation

Figure 9A:
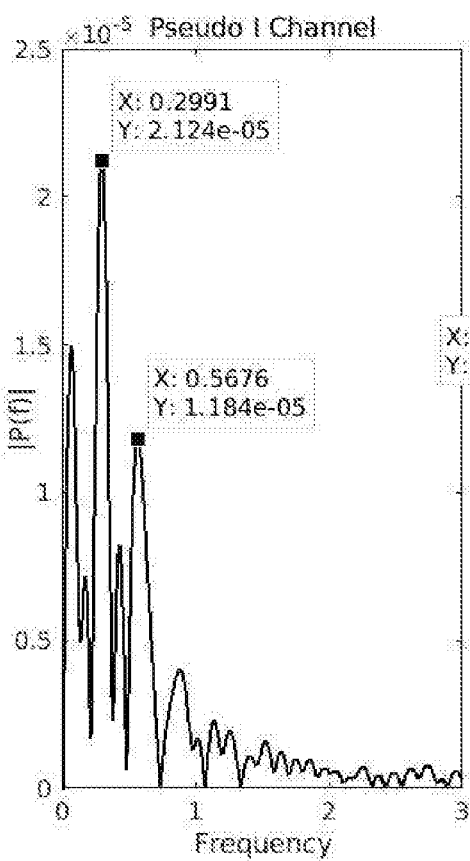
FIG. 9A and FIG. 9B illustrate a frequency spectrum of a pseudo I channel and a pseudo Q channel respectively for an experimental data set.
Figure 9B:
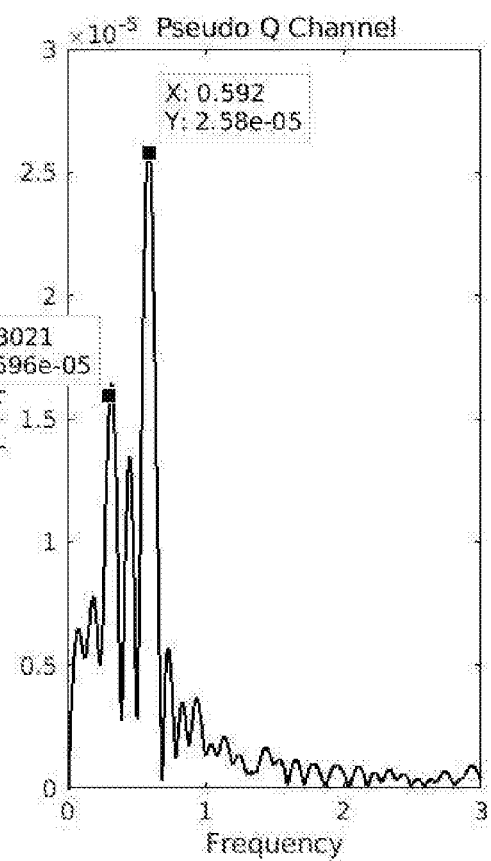
Figure 9C:
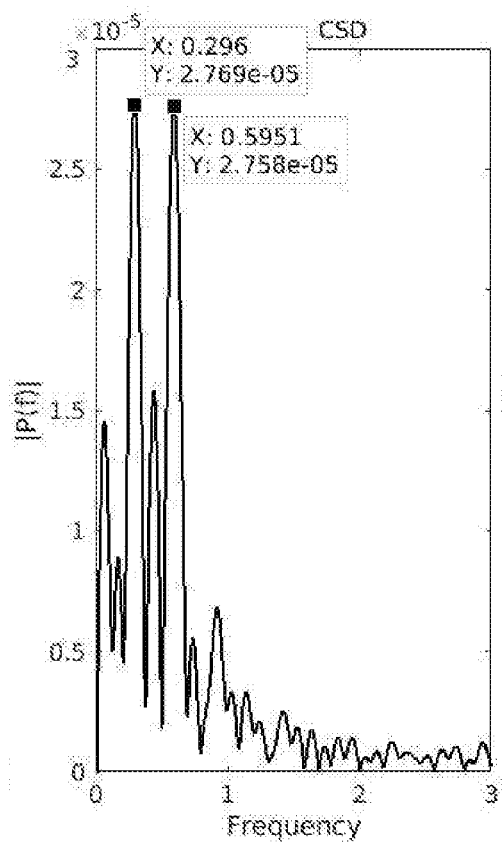
FIG. 9C illustrates a frequency spectrum using a Complex Signal Demodulation (CSD) method as known in the art on the experimental data set.
Figure 9D:
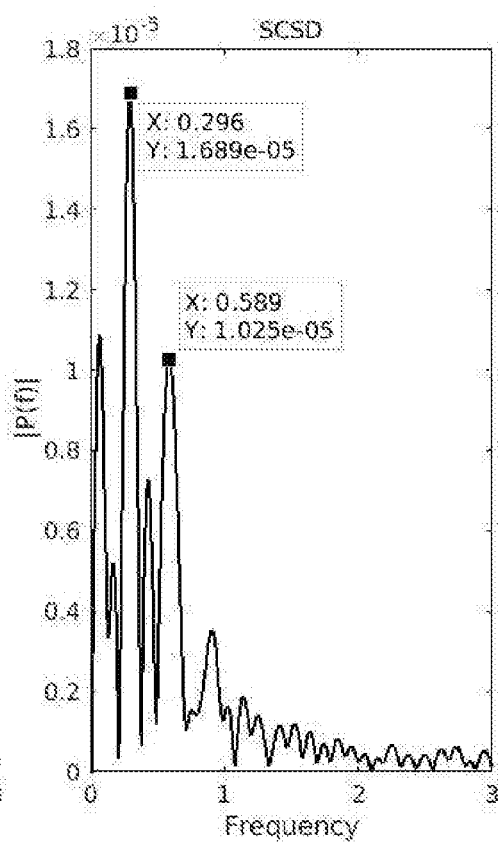
FIG. 9D illustrates a frequency spectrum using the Supervised Complex Signal Demodulation (SCSD) method of the present disclosure.

Physiological signals, are very low amplitude band-limited signals. Adding up the harmonics can lead to false detection of the vital signs. 20 sets of data were collected. FIG. 9A and FIG. 9B illustrate a frequency spectrum of the pseudo I channel and the pseudo Q channel respectively for the experimental data set. The observed breathing rate for a subject being monitored was around 0.29 Hz (18 breaths/minute) and the corresponding harmonics was around 0.59 Hz. Due to amplitude imbalance, the harmonics had comparable signal strength. FIG. 9C illustrates a frequency spectrum using the CSD method as known in the art on the experimental data set, wherein both the harmonics and fundamental frequencies are almost equal. Depending on the frequency spectrum pattern, the SCSD method of the present disclosure was applied. It was noted that the pseudo I channel was labelled as the 'better optimum class' and the pseudo Q channel was labelled as the 'better null class'. Accordingly, weights were assigned to both the channels to suppress the effect of amplitude imbalance. FIG. 9D illustrates a frequency spectrum using the SCSD method of the present disclosure, wherein the fundamental frequency is clearly visible as compared to the harmonics.

Systems and methods of the present disclosure thus provide a simple, unobtrusive and cost effective solution for real time monitoring of physiological signals such as breathing rate and heart rate using the indented radar system comprising pseudo IQ radars. The standard CSD method fails to detect actual vibrational frequencies when applied on the indented radar system. Hence, in accordance with the present disclosure, the SCSD method is provided to suppress the effect of amplitude imbalance.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for real time unobtrusive monitoring of physiological signals pertaining to a subject confined to a bed (200), the method comprising the steps of:
    obtaining periodically, by one or more hardware processors, a motion data signal pertaining to the physiological signals including heartbeat rate and breathing rate from the subject, from a pseudo I (in-phase) channel and a pseudo Q (in quadrature) channel of three pseudo IQ radars, wherein the three pseudo IQ radars are positioned in a predetermined configuration around the subject and wherein each of the three pseudo IQ radars comprise a pair of single channel continuous wave (CW) radars placed at a calibrated distance from each other such that optimum points of one CW radar in the pair spatially overlaps null points of the other CW radar in the pair, a baseband signal from the CW radars constituting the pair serving as the pseudo I channel and the pseudo Q channel respectively (202);
    processing, by the one or more hardware processors, the motion data signal from each of the three pseudo IQ radars, to discard the motion data signal having motion artifacts (204);
    determining, by the one or more hardware processors, Quality of Information (QoI) based on at least one of Signal to Noise Ratio (SNR) and frequency spectrum associated with the motion data signal from each of the three pseudo IQ radars having no motion artifacts (206), wherein the QoI is indicative of the pseudo IQ radar from the three pseudo IQ radars to be considered for each lying position of the subject such that readings corresponding to the motion data signal have maximum SNR and minimum harmonic content;
    recalibrating, by the one or more hardware processors, one or more of the three pseudo IQ radars if the readings corresponding to the motion data signal having no motion artifacts deviate from an empirically determined threshold, wherein the threshold is indicative of number of times anomalous readings are received from the pseudo I channel and the pseudo Q channel (208); and
    evaluating, by the one or more hardware processors, the heartbeat rate and breathing rate by applying a Supervised Complex Signal Demodulation (SCSD) method on the motion signal data received from the one or more of the three pseudo IQ radars based on the QoI (210), wherein the SCSD method is configured to suppress amplitude and DC imbalance by assigning weights to the pseudo I channel and the pseudo Q channel, the weights being determined using a simulated trained weighted K-Nearest Neighbor (KNN) model configured to identify reliability of the pseudo I channel and the pseudo Q channel based on Fast Fourier Transform (FFT) pattern thereof in the range of the heartbeat rate and breathing rate, the reliability being indicative of harmonic content in the motion signal data, wherein the simulated trained weighted K-Nearest Neighbor (KNN) model is trained using training data simulated by:
    dividing the calibrated distance into a plurality of bins including points ranging from the optimum points to the null points;
    further dividing each of the plurality of bins into five classes including null class, better null class, middle class, better optimum class and optimum class having a distinct frequency spectrum therein;
    identifying a frequency band of operation corresponding to the physiological signal being monitored;
    simulating for each of the five classes comprised in each of the plurality of bins, the baseband signal for incremental steps of all frequencies in the frequency band of operation and incremental distances corresponding to each of the five classes;
    generating features including location of peaks and peak to peak ratio from frequency plots using the simulated baseband signal for each of the five classes comprised in each of the plurality of bins; and
    training the weighted KNN model using the generated features for each of the five classes comprised in each of the plurality of bins.

2. The processor implemented method of claim 1, wherein the predetermined configuration provides maximum beam coverage of the bed and comprises two of the three pseudo IQ radars positioned over the subject and one of the three pseudo IQ radars positioned below the bed such that the three pseudo IQ radars form an isosceles triangle for obtaining the motion data signal unobtrusively regardless of the lying position of the subject on the bed.

3. The processor implemented method of claim 1, wherein the calibrated distance is based on wavelength of the CW radars comprising the three pseudo IQ radars.

4. The processor implemented method of claim 3, wherein the calibrated distance is an integer (n) multiple of one eighth of the wavelength ($\lambda/8$) of the CW radars comprising the three pseudo IQ radars.

5. The processor implemented method of claim 1, wherein the presence of motion artifacts is detected when dominant frequency in the motion signal data is beyond 2 Hz.

6. The processor implemented method of claim 1, wherein the step of recalibrating one or more of the three pseudo IQ radars comprises suppressing phase imbalance between the pseudo I channel and the pseudo Q channel by fine adjustment of the calibrated distance between the CW radars constituting the pair.

7. A system (100) for real time unobtrusive monitoring of physiological signals pertaining to a subject confined to a bed, the system comprising:
    an indented radar system (102) comprising three pseudo IQ radars positioned in a predetermined configuration around the subject, wherein each of the three pseudo IQ radars comprises a pair of single channel continuous wave (CW) radars placed at a calibrated distance from each other such that optimum points of one CW radar in the pair spatially overlaps null points of the other CW radar in the pair, a baseband signal from the CW radars constituting the pair serving as a pseudo I (in-phase) channel and a pseudo Q (in quadrature) channel respectively; and
    a controller unit (104) in communication with each of the three pseudo IQ radars, wherein the controller unit comprises:
        one or more data storage devices (104A) configured to store instructions; and
        one or more hardware processors (104B) operatively coupled to the one or more data storage devices, wherein the one or more hardware processors are configured by the instructions to:
            obtaining periodically, a motion data signal pertaining to the physiological signals including heartbeat rate and breathing rate from the subject, from the pseudo I channel and the pseudo Q channel of the three pseudo IQ radars;

processing the motion data signal from each of the three pseudo IQ radars, to discard the motion data signal having motion artifacts;

determining Quality of Information (QoI) based on at least one of Signal to Noise Ratio (SNR) and frequency spectrum associated with the motion data signal from each of the three pseudo IQ radars having no motion artifacts, wherein the QoI is indicative of the pseudo IQ radar from the three pseudo IQ radars to be considered for each lying position of the subject such that readings corresponding to the motion data signal have maximum SNR and minimum harmonic content;

recalibrating one or more of the three pseudo IQ radars if the readings corresponding to the motion data signal having no motion artifacts deviate from an empirically determined threshold, wherein the threshold is indicative of number of times anomalous readings are received from the pseudo I channel and the pseudo Q channel; and evaluating the heartbeat rate and breathing rate by applying a Supervised Complex Signal Demodulation (SCSD) method on the motion signal data received from the one or more of the three pseudo IQ radars based on the QoI, wherein the SCSD method is configured to suppress amplitude and DC imbalance by assigning weights to the pseudo I channel and the pseudo Q channel, the weights being determined using a simulated trained weighted K-Nearest Neighbor (KNN) model configured to identify reliability of the pseudo I channel and the pseudo Q channel based on Fast Fourier Transform (FFT) pattern thereof in the range of the heartbeat rate and breathing rate, the reliability being indicative of harmonic content in the motion signal data, wherein the one or more hardware processors are further configured by the instructions to perform training of the simulated trained weighted K-Nearest Neighbor (KNN) model using training data simulated by:

dividing the calibrated distance into a plurality of bins including points ranging from the optimum points to the null points;

further dividing each of the plurality of bins into five classes including null class, better null class, middle class, better optimum class and optimum class having a distinct frequency spectrum therein;

identifying a frequency band of operation corresponding to the physiological signal being monitored;

simulating for each of the five classes comprised in each of the plurality of bins, the baseband signal for incremental steps of all frequencies in the frequency band of operation and incremental distances corresponding to each of the five classes;

generating features including location of peaks and peak to peak ratio from frequency plots using the simulated baseband signal for each of the five classes comprised in each of the plurality of bins; and training the weighted KNN model using the generated features for each of the five classes comprised in each of the plurality of bins.

8. The system of claim 7, wherein the predetermined configuration provides maximum beam coverage of the bed and comprises two of the three pseudo IQ radars positioned over the subject and one of the three pseudo IQ radars positioned below the bed such that the three pseudo IQ radars form an isosceles triangle for obtaining the motion data signal unobtrusively regardless of the lying position of the subject on the bed.

9. The system of claim 7, wherein the calibrated distance is based on wavelength of the CW radars comprising the three pseudo IQ radars.

10. The system of claim 9, wherein the calibrated distance is an integer (n) multiple of one eighth of the wavelength ($\lambda/8$) of the CW radars comprising the three pseudo IQ radars.

11. The system of claim 7, wherein the presence of motion artifacts is detected when dominant frequency in the motion signal data is beyond 2 Hz.

12. The system of claim 7, wherein the one or more hardware processors are further configured by the instructions to perform recalibrating one or more of the three pseudo IQ radars by suppressing phase imbalance between the pseudo I channel and the pseudo Q channel by fine adjustment of the calibrated distance between the CW radars constituting the pair.

* * * * *